United States Patent
May et al.

(10) Patent No.: US 6,398,724 B1
(45) Date of Patent: Jun. 4, 2002

(54) FOCUSABLE OPTICAL INSTRUMENT WITH A SEALED OPTICAL SYSTEM HAVING NO INTERNAL OPTICAL MOVING PARTS

(75) Inventors: Kevin Brent May, Yorba Linda; Ketan K. Pandya, Fullerton; Alex Vayser, Mission Viejo, all of CA (US)

(73) Assignee: Medivision, Inc., Anaheim, CA (US)

( * ) Notice: Subject to any disclaimer, the term of this patent is extended or adjusted under 35 U.S.C. 154(b) by 0 days.

(21) Appl. No.: 09/527,499

(22) Filed: Mar. 16, 2000

(51) Int. Cl.7 .................................................. A61B 1/04
(52) U.S. Cl. ...................................... 600/167; 600/112
(58) Field of Search .............................. 600/112, 163, 600/167, 168, 172; 359/822, 823, 825, 826

(56) References Cited

U.S. PATENT DOCUMENTS

| | | | | |
|---|---|---|---|---|
| 4,569,333 A | * | 2/1986 | Bel et al. ..................... 600/133 |
| 4,742,818 A | * | 5/1988 | Hughes et al. ............... 600/133 |
| 4,905,668 A | * | 3/1990 | Ohsawa ........................ 348/65 |
| 5,191,879 A | * | 3/1993 | Krauter ....................... 600/109 |
| 5,528,432 A | * | 6/1996 | Donahoo ...................... 348/66 |
| 5,575,757 A | | 11/1996 | Kennedy | |
| 5,599,278 A | | 2/1997 | Hibbard | |
| 5,702,350 A | * | 12/1997 | Vry et al. .................... 600/166 |
| 5,745,165 A | * | 4/1998 | Atsuta et al. ................. 348/65 |
| 5,797,836 A | * | 8/1998 | Lucey et al. ................ 600/109 |
| 5,846,186 A | * | 12/1998 | Upsher ........................ 600/112 |
| 5,879,289 A | * | 3/1999 | Yarush et al. ............... 600/109 |
| 5,895,350 A | * | 4/1999 | Hori ............................ 600/109 |
| 6,019,719 A | | 2/2000 | Schulz | |
| 6,069,651 A | * | 5/2000 | Tsuyuki et al. .............. 348/65 |

* cited by examiner

Primary Examiner—John P. Leubecker
(74) Attorney, Agent, or Firm—K. David Crockett, Esq.; Crockett & Crockett

(57) ABSTRACT

An endoscope having an autoclavable replaceable sealed optical assembly without moveable parts. The sealed optical assembly is placed into an insertion tube of the endoscope. A focusing device is attached to the proximal end of the sealed optical assembly. The opposite end of the focusing device may be connected to an appropriate image-receiving device such as a CCD camera. The endoscope differs from conventional optical devices of this type in that its focusing is performed by shifting the image-receiving plane of the CCD camera with respect to an immobile plane of a image produced by optical elements of the sealed optical assembly.

24 Claims, 6 Drawing Sheets

FOCUSABLE OPTICAL INSTRUMENT WITH A SEALED OPTICAL SYSTEM HAVING NO INTERNAL OPTICAL MOVING PARTS

FIELD OF THE INVENTION

The present invention relates to the field of optics, in particular to focusable optical instruments for observation within confined spaces such as internal cavities of a human body. In particular, the invention relates to a medical endoscope. An endoscope is an instrument for the visual examination of the interior of a body cavity or viscus. Endoscopes have become widely utilized in surgery to permit performance of diagnostic and surgical procedures internally without the need for invasive surgical procedures. An endoscope is typically inserted through a small incision portal providing access to the body cavity. A lens at a distal end of the endoscope is positioned to receive light reflected from a site to be observed, and images of the site can be viewed remotely to conduct histological examinations and to perform closed, or endoscopic, surgery. As used herein, the term endoscope refers generically to viewing devices for remotely observing otherwise inaccessible body cavities with minimal trauma and intrusion, including but not limited to arthroscopes, colonoscopes, bronchoscopes, hysteroscopes, cystoscopes, sigmoidoscopes, laparoscopes, sinoscopes, small-joint dental scopes, ureterscopes, etc.

A typical endoscope includes an elongated flexible or rigid outer tube within which a lens system is disposed at a distal end. The image of the object being viewed by the optical system is transmitted through an optical system from the distal end to a proximal end of the tube for viewing by the user or for reception by a camera. Some endoscopes also carry fiber optic cables for illuminating the area of observation with light supplied by an external source.

One endoscope with a typical focusing mechanism is disclosed, e.g., in U.S. Pat. No. 5,575,757 issued in 1996 to Kennedy, et al. As shown in FIGS. 1 and 2, where FIG. 1 is a sectional view of a distal end and FIG. 2 is a sectional view of a proximal end of the endoscope of U.S. Pat. No. 5,575,757, the endoscope, which is designated as a whole by reference numeral 10, includes an elongated insertion section 12 for insertion into a body cavity or narrow body passage to observe an object therein (not shown). Elongated insertion section 12 extends along a longitudinal axis 13 of endoscope 10 from a distal end 14 to a handle 16 at the proximal end 19 of endoscope 10. Handle 16 permits the user to position elongated insertion section 12 of endoscope 10 appropriately and also houses a focus control mechanism 17 for endoscope 10, which is described in detail below. A cable 18 extends from proximal end 19 for connection to a power source and camera control unit (not shown). Images observed at distal end 14 of endoscope 10 are processed by the video processor for viewing on a display unit.

Elongated insertion section 12 includes an outer tube 20 for housing an objective lens assembly 22, an image transmitting device, e.g., an electro-optic module 23, having an electro-optical sensor 24 (e.g. a charge-coupled device (CCD)) for converting optical images of the received light into electrical image signals), and light guiding fiber optic elements 26 for illuminating the area being observed. Outer tube 20 extends from distal end 14 of endoscope 10 to a first end of a main housing 30 at handle 16 where tube 20 is soldered within a counterbore of main housing 30.

Elongated insertion section 12 further includes an inner cylindrical tube 31 and a CCD tube 32, each coaxially disposed within outer tube 20. Inner cylindrical tube 31 extends from the distal end 14 of the outer tube 20 to an enlarged proximal end 31a that receives the distal end of CCD tube 32. Tube 31 is radially spaced from outer tube 20 to provide a cylindrical passage within which fiber optic elements 26 pass to distal end 14. CCD tube 32 is shown having a first cylindrical member 33 extending from a region directly behind lens assembly 22 to a region partially within main housing 30 and a second extension member 34 soldered to first cylindrical member 33 which extends to focus control mechanism 17. The distal end 33a of CCD tube 32 has a pair of enlarged diameter regions 29a, 29b as shown to receive electro-optic module 23 and a crimped end of cable 18, respectively. Electro-optic module 23 is secured into region 29a of CCD tube 32 with epoxy. Cable 18 has a woven ground conductor surrounded by a band 21, which is crimped to prove a snug fit within region 29b.

Referring to FIG. 2, focus control mechanism 17 allows a user to focus endoscope 10 by adjusting the distance between objective lens assembly 22 and CCD 24, e.g., by ±0.1 mm. As mentioned above, objective lens assembly 22 and CCD 24 are rigidly secured to inner tube 31 and CCD tube 32, respectively. The spacing between CCD 24 and lens assembly 22 is varied by moving CCD tube 32 axially along longitudinal axis 13 of endoscope 10. The front face 25 of CCD 24 is moved by focus control mechanism 17 in response to rotation of focus ring 80 by the user.

Main housing 30 has a through hole 46 extending its length to receive CCD tube 32 and to allow cable 18 to pass through endoscope 10. A pair of oblong slots 48, 50 are disposed through opposite sidewalls of an end portion 65 of main housing 30 for respectively receiving a pair of cam screws 76, 78.

A cylindrical actuator 62 is interposed between main housing 30 and CCD tube 32 and is threaded to receive the proximal end of CCD tube 32. A pair of threaded holes 66, 67 orthogonal to axis 13 are disposed through the walls of actuator 62 and are aligned with oblong slots 48, 50 of main housing 30. A lock nut 63 secures actuator 62 to the proximal end of CCD tube 32.

Along an outer surface of main housing 30 is a cylindrical focus sleeve 68 having a pair of diametrically opposed helical grooves 70, 71 each of which is aligned with a corresponding one of threaded holes 66, 67 of actuator 62 and a corresponding one of oblong slots 48, 50. Each one of a pair of cam bearings 74 having through holes 77 engages a corresponding one of helical grooves 70, 71 and contacts actuator 62 along diametrically opposite helical surfaces of slots 70, 71.

To disassemble focus control mechanism 17, rear housing 102 is unscrewed from the rear portion of main housing 30 and with retainer 104 is drawn along cable 18. Focus ring 80 axially separated from focus sleeve 68 by applying a sufficient force proximally along the length of handle 16 sufficient to separate pin 82 from hole 85 focus sleeve 68. With focus ring 80 removed, cam screws 76, 78 are exposed and can be unscrewed from actuator 62 allowing cam bearings 74 to be removed from through holes 77 of focus sleeve 68. With cam bearings 74 removed, focus sleeve 68 can be slid off of the end of main housing 30.

Thus, by rotating focus control mechanism 17, the user shifts the front face 25 of CCD 24 relative to the objective lens assembly 22 due to interaction of the actuator 62 with helical slots 70 and 71.

The endoscope of U.S. Pat. No. 5,575,757 described above is characterized by the following disadvantages. First of all, the distal end 12 of the endoscope, which is insertable into the human body has a complicated construction as it contains the entire objective optical assembly 22 and moving parts of the focusing mechanism, i.e., the image-sensing device 24. In other words, the image-sensing device 24 is an integral part of the endoscope itself This means, that the endoscope of U.S. Pat. No. 5,575,757 is inapplicable as an attachment to an external image sensing device such as a CCD camera connected to a monitor. At the same time, modern clinics are normally equipped with external image sensing devices, which are widely used in practice. Furthermore, the endoscope of U.S. Pat. No. 5,575,757 has a plurality of threaded connections and seals, so that disconnection of the disposable part is a time consuming operation. Disassembling procedure is accompanied by violation of sealing conditions inside the endoscope.

The endoscope of the aforementioned construction is not autoclavable as an integral unit, as it has relatively movable inner parts. It is stated in the aforementioned patent that the insertable portion, i.e., the distal end 12, is disposable. Thus, an expensive part of the entire unit that contains objective optical assembly and the image-sensing device is disposed after the first use.

Attempts have been made to provide autoclavable endoscopes that can be sterilized without disassembling. One such construction is disclosed in U.S. Pat. No. 5,599,278 issued in 1997 to E. Hibbard. This autoclavable endoscope has a housing, an eyepiece, an insertion tube, proximal and distal windows, and seals that seal against the passage of contaminants into the endoscope during autoclaving. The housing, eyepiece, insertion tube, windows and light pipe are comprised of materials, which withstand a temperature of at least about 650° C. (1200° F.). However, this endoscope does not have a focusing mechanism, which is a significant disadvantage.

One of the most recent inventions in U.S. Pat. No. 6,019,719 issued to D. Schulz in February of 2000 relates to an electronic endoscope with a semiconductor image sensor (CCD chip) for receiving the images received by an objective. The endoscope has an electronic circuit and comprises a shaft with a distal end and a proximal end, and the objective and CCD chip which are arranged at the distal end. The proximal end is held in a housing, which holds the shaft and encloses the glass-fiber optical connection. The component parts of the CCD chip unit arranged behind the objective, namely the crystal filter, IR cutoff filter and CCD chip, are arranged so as to be spaced from one another. This endoscope is autoclavable and has focusing capability performed electronically. However, this endoscope has extremely sophisticated and expensive construction that envisage insertion of the miniature visualizing device together with associated signal processing equipment into the human body.

OBJECTS OF THE INVENTION

It is an object of the present invention to provide a focusable endoscope which is autoclavable as an integral unit, has an entirely sealed autoclavable optical assembly, has no internal moving optical components, is provided with an external focus adjustment sealed independently of the optical system, is characterized by an entirely reusable construction as a whole, has an image plane outside of the endoscope enclosure, is inexpensive to manufacture, easy to use, easy to assembly and disassemble, has an optical performance which is not affected in case of damage of the seals, and is compatible with a variety of existing external image-sensing devices.

SUMMARY OF THE INVENTION

The focusable optical instrument of the invention is illustrated in the form of an endoscope which consists of a sealed encapsulated optical assembly unit having no internal moveable parts and a focusing assembly combined with an external image sensing device such as a CCD camera attached to the focusing assembly for moving with the focusing assembly as an integral unit. The encapsulated optical assembly unit contains various optical elements, which receive the image from the object being observed, and transmit the obtained object to the external image sensing device. The distinguishing feature of the invention is that the optical system has no moving parts and therefore can be sealed and encapsulated. In view of the above, the optical system can be autoclaved as an integral unit without disassembling. In contrast to a conventional endoscope system in which focusing is achieved by moving elements of the optical system with respect to each other, the endoscope of the invention is focused by shifting the encapsulated optical assembly as a whole with respect to the external image sensing device.

DETAILED DESCRIPTION OF THE INVENTION

Figure 1:
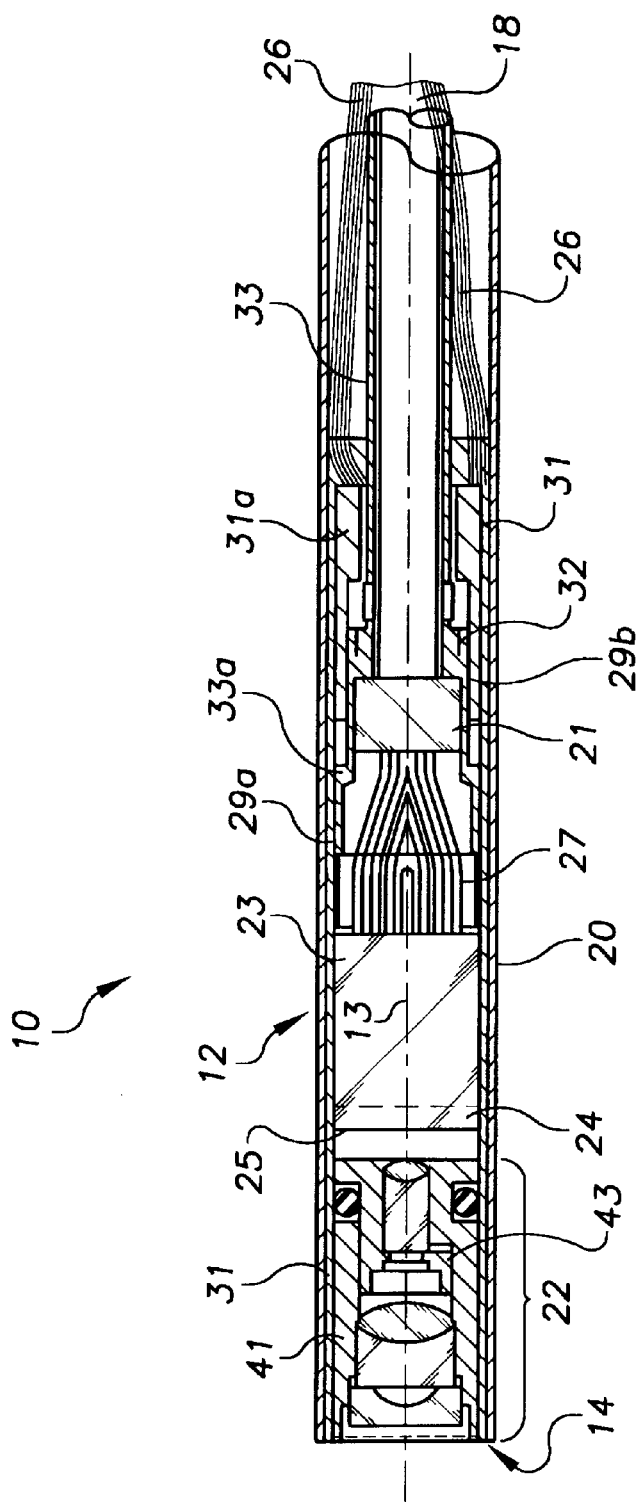
FIG. 1 is a sectional view of a distal end of a known endoscope.
Figure 2:
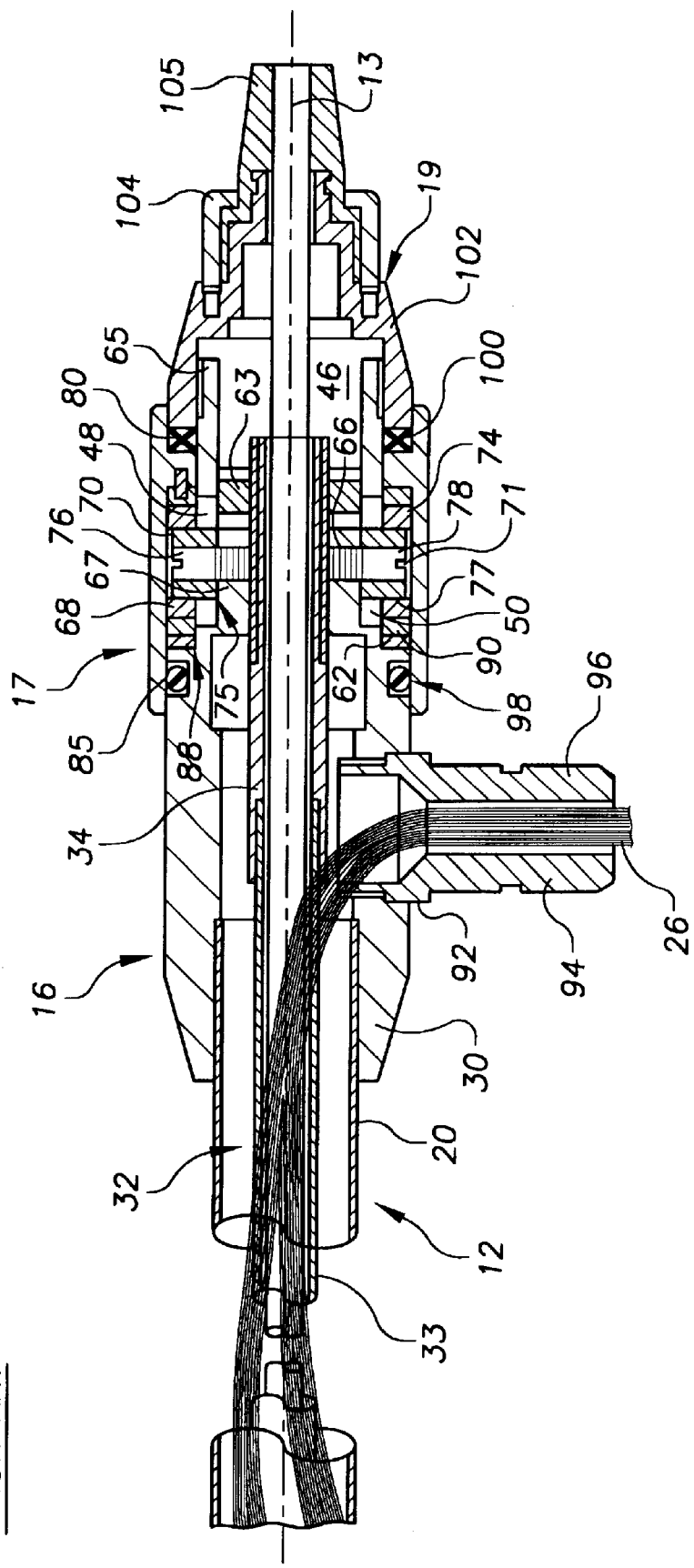
FIG. 2 is a sectional view of a proximal end of a known endoscope.
Figure 3:
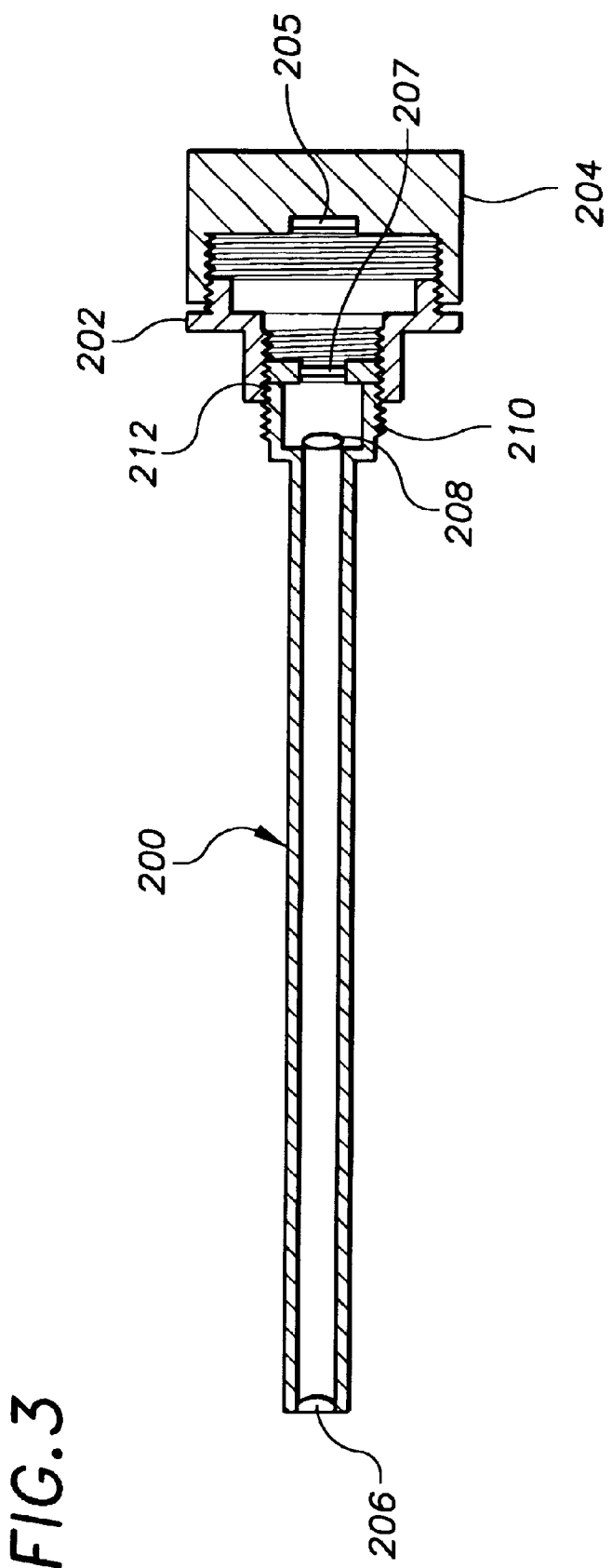
FIG. 3 is a schematic view of an endoscope made in accordance with one embodiment of the invention.

In its simplest form, the optical instrument of the invention will be described as an endoscope shown schematically in FIG. 3. It consists of two principle units having relative movement with respect to one another, i.e., a sealed encapsulated optical assembly unit 200 having no moveable parts and a focusing assembly 202 combined with an external image sensing device 204 such as a CCD camera, a still camera, or another image-receiving device attached to the focusing assembly 202 for moving with the focusing assembly as an integral unit. The encapsulated optical assembly unit 200 has an image collecting element, e.g., an objective 206 at its distal end and an image output element, e.g., an ocular 208 on its proximal end. The ocular 208 is hermetically closed with a light-permeable sealed window 207.

The external image sensing device 204 has an image-receiving plane 205 which may be the front image-receiving plane of a CCD camera. In a simplest embodiment shown in FIG. 3, the sealed encapsulated optical assembly unit 200 has an external thread 210, whereas the focusing assembly 202 has an internal thread 212 engaged with the external thread 210 so that rotation of the focusing unit 202 on the sealed encapsulated optical assembly unit 200 will change the distance L1 between the ocular 208 and the image-receiving plane 205.

Thus, it has been shown that in contrast to a conventional endoscope system, in the system of the invention, focusing is achieved by shifting the encapsulated optical assembly, which has no internal moving parts, with respect to the external image sensing device. In other words, focusing can be done without changing the distance between the ocular and the relay optics.

Figure 4:
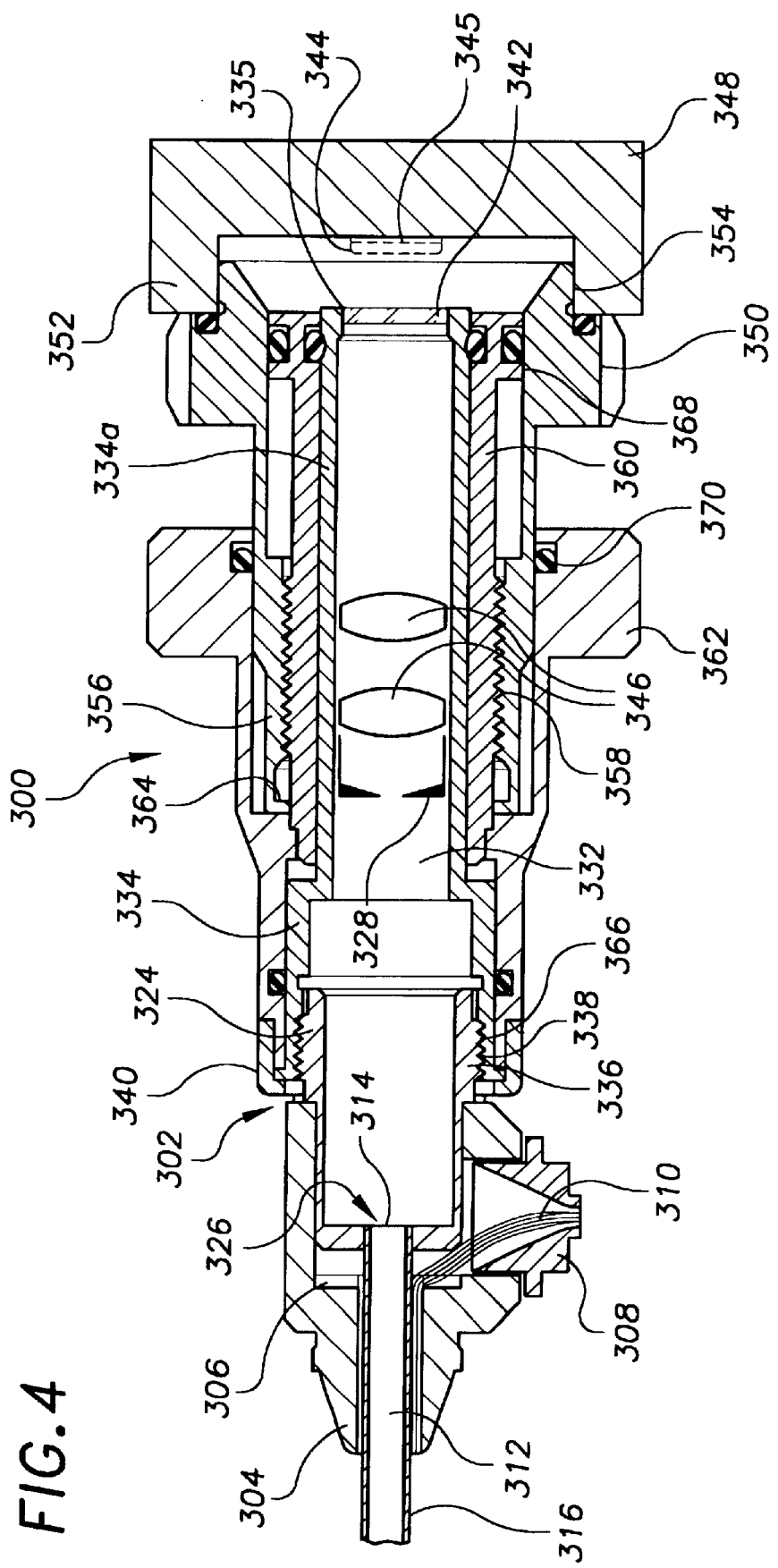
FIG. 4 is a schematic view of a proximal end of an endoscope made in accordance with another embodiment of the invention.
Figure 5:
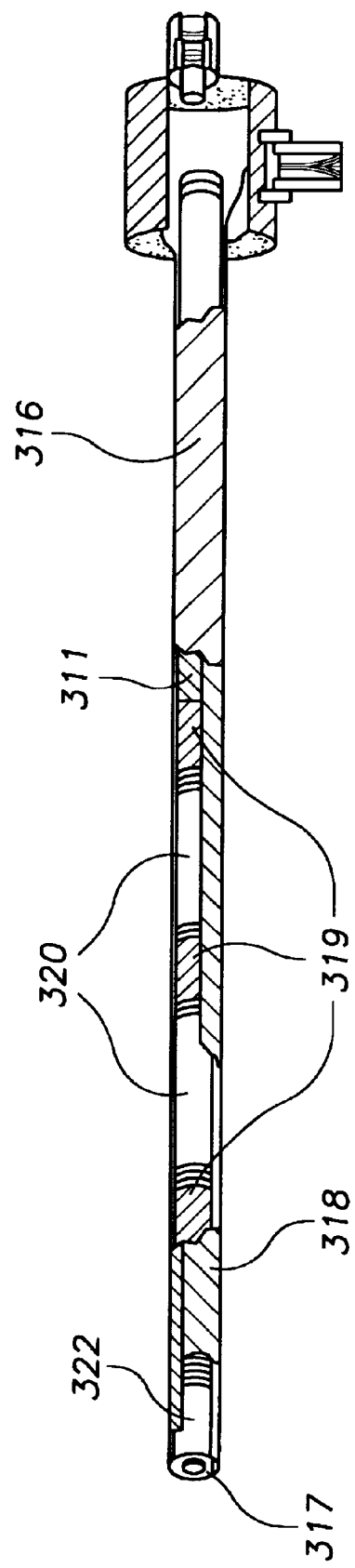
FIG. 5 is a three-dimensional view of a distal end of the endoscope of FIG. 4.

The invention will now be described in more detail with reference to a preferred embodiment shown in FIGS. 4 and 5, where FIG. 4 is a longitudinal sectional view of the endoscope, and FIG. 5 is a three-dimensional partially-broken view of a distal end of the endoscope. As shown in the drawings, the proximal end of the endoscope consists of a focusing-coupling system 300; which houses a sealed optical assembly 302. In the illustrated embodiment, the sealed optical assembly 302 consists of an insertion tube holder 304 having a cup-shaped configuration with a central hole at one end and a large-diameter bore 306 on the opposite side. A light port 308 may be formed in a sidewall of the insertion tube holder 304 for attaching a lighting device such as a fiber cable 310, which illuminates a proximal end of a light-conducting element. This is shown by reference numeral 311 in the form of braiding composed of a plurality of light-conducting optical fibers covering the entire inner surface of the insertion tube 316 (FIG. 4 and FIG. 5).

As shown in FIG. 5, the optical rod 314 is contained in an insertion tube 316 that constitutes the distal end 318 of the endoscope, which is insertable into the body of a patient. It can be seen that in the illustrated embodiment the optical rod is only one element of the sealed optical assembly 302 which, apart from the optical rod 314, contains a number of other optical elements arranged in series in the direction toward the very tip of the distal end, i.e., spacers 319, rod lenses 320, and objective 322. It is understood that all these optical elements are shown only for illustrative purposes and that the optical system may have a variety of arrangements and components, depending on a specific application of the endoscope. What is important to mention is that the interior of the insertion tube 316 is hermetically sealed. For this purpose, the end of the objective 322 which is exposed to the outside of the tube is soldered, brazed, or welded to the tube 316 with a hermetic weld seam 317. The material of the solder, as well as the materials of the optical components 314, 319, 320, 322, and of the insertion tube 316 should withstand autoclaving temperature up to 134° C. (274° F.). Examples of such materials are tin-silver solder, epoxy-type adhesive, or the like.

The proximal end of the insertion tube 316 is also soldered to the walls of the central opening 304 of the insertion tube holder 304 with a hermetic seal or weld. The proximal end of the insertion tube 316 with the optical rod 314 is further supported by a hollow eyepiece optic mount 324. For this purpose, the proximal end of the insertion tube 314 is inserted into the opening 326 of the hollow eyepiece optic mount 324 and also is hermetically sealed by soldering or welding to the walls of the opening 326. The end of the hollow eyepiece optic mount is connected to an optics barrel 334.

The front end of the optics barrel 334 has an internal thread 336 screwed onto the external thread 338 on the eyepiece optic mount 324. Sealing conditions in the threaded connection can be provided by an O-ring placed between the optics barrel 334 and the eyepiece optic mount 324 and pressed against the retaining ring 340 inserted into the annular groove in the outer surface of the eyepiece optic mount 324. Alternatively, the optics mount 324 and the optics barrel 334 can be soldered together, welded, or glued, e.g., with an epoxy adhesive, to achieve a hermetic seal.

The optics barrel 334 has an elongated small-diameter portion 334a, which extends in the direction opposite to the insertion tube 316. The rear end of the optical barrel 334 is hermetically closed by a glass plate 342, which is permeable to light. The elongated small-diameter portion 334a contains an image plate 328 which functions as a field stop and which is located in from of the image coupling system, e.g., in the form of a simple telescope 346, which is schematically shown in the form of two lenses. It is important to notice that the proximal end of the optics barrel 334 should be reliably sealed to protect the interior of this barrel from penetration of liquids and contaminants during autoclaving at temperatures as high as 650° C., though in real practice autoclaving is conducted at a temperature of about 134° C.

High resistance to temperature is achieved due to the fact the glass plate 342 has a metallized edges which allow brazing, welding, or soldering of the glass plate 342 to the rear end face of the barrel 334. The solder or welding seam 335 can be represented by tin-silver solder, or a similar material.

The image reproduced on the image plate 328 is projected through the image coupling system 346 to the image plane 344. When the endoscope is focused, this image plane 344 coincides with the front surface 345 of a CCD camera. This camera is shown schematically in FIG. 3 and is designated by reference numeral 348.

The focusing coupling system 300 is further provided with a camera adapter 350, which connects the sealed optical assembly 302 with the CCD camera 348. In the illustrated embodiment, the camera adapter 350 has threaded connection with the CCD camera, although connection of any other type, e.g., a bayonet-type connection is also possible. As shown in FIG. 4, the camera adapter 350 has an external thread 352 on its proximal end, whereas the CCD camera 348 has an internal thread 354 into which the thread 352 is screwed. The distal end of the camera adapter 350 has an internal thread 356, which is threaded onto an external thread 358 formed on the outer surface of an internal driver 360. The internal driver 360 is made in the form of a sleeve, which is slidingly fit onto the outer surface of the optics barrel: The distal end of the internal driver 360 is rigidly connected to a focus driver 362, which is made in the form of a sleeve with a flange 364. The connection between the internal driver 360 and the focus driver 362 can be made in the form of an internal thread 364 in the focus driver 362 and the external thread 366 on the distal end of internal driver 360. The focus driver 362, in turn, is rigidly connected to the optical assembly unit 302.

To avoid contamination of the internal mechanical elements of the focusing assembly 300, as well as contamination of other internal parts such as threaded portions, sliding surfaces, etc., during autoclaving under elevated temperatures of about 134° C., the connections between the part are sealed with heat-resistant seals that can withstand the above temperature. Examples of such seals are Teflon-encapsulated O-rings commercially produced by M-COR Inc., Co., Woodale, Ill.

In the embodiment shown in FIG. 4, connection between the internal driver 360 and the camera adapter 350 is sealed by an O-ring 368. Sliding fit between the focus driver 362 and the camera adapter 350 is sealed by an O-ring 370. As has been mentioned above, other seals can be made by hermetic welding, soldering, or adhesives.

Figure 6:
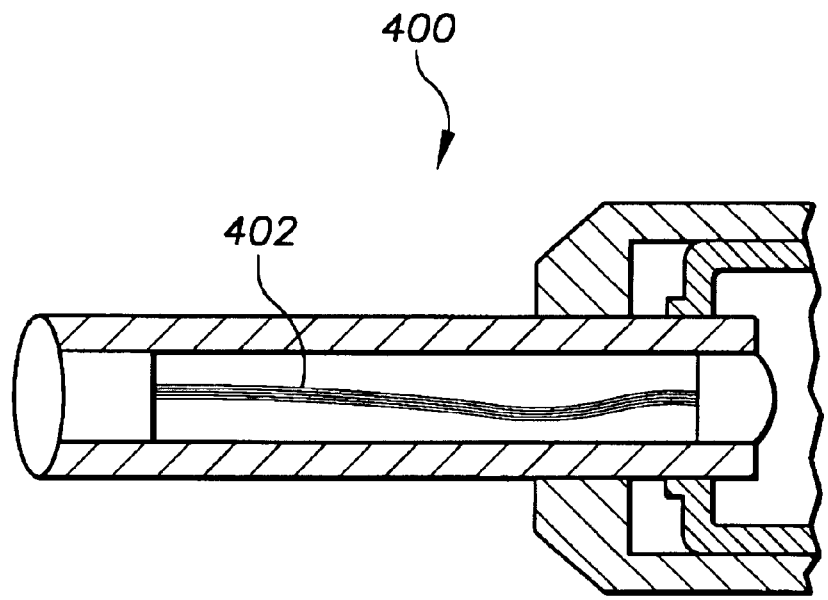
FIG. 6 is a partial sectional view of the distal end of the endoscope of the invention with an optical element in the form of an optical fiber.

FIG. 6 illustrates another embodiment of the invention which is a partial view of the distal end of an endoscope 400, which in general is the same as the one shown in FIGS. 4 and 5 and differs from it by using an optical fiber 402 instead of optical rods shown in the embodiment of FIGS. 4 and 5. The use of an optical fiber 402 is advantageous in that it allows flexibility of an insertion tube 404 which can be made of a flexible medically-acceptable material.

Figure 7:
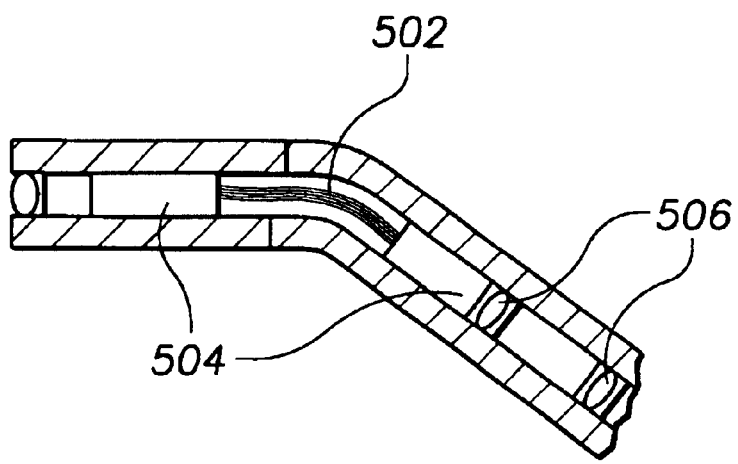
FIG. 7 is a partial sectional view of the distal end of the endoscope of the invention with an optical element comprising a combination of optical rods with optical fibers and lenses.

FIG. 7 illustrates another embodiment of the invention which is a partial view of the distal end of an endoscope 500 which in general is the same as the one shown in FIG. 6 and differs from it by using an image delivery system which combines in itself an optical fiber 502 with an optical rod 504 (or rods) and lenses 506.

In operation, the insertion tube 316 is inserted into the lumen of a human body or into the internal organ through an incision, as required by the treatment or surgery procedure. The physician then holds the focus driver 362 as a handle and adjusts the focus of the image obtained from the area of interest by rotating the camera adapter 350. This rotation changes the distance between the sealed optical assembly 302, and hence between the image plane 344 produced by the optical system, and the image receiving plane 345 of the image sensing device 348.

Upon completion of the treatment or surgery, the endoscope can be easily disconnected from the CCD camera 348 and autoclaved as a whole or partially. For partial autoclaving or for replacements of the parts, the optical assembly 302 is disconnected from the focusing unit by unscrewing the retaining ring 340 from the focus driver 362.

Thus it has been shown that the present invention provides a focusable endoscope which is autoclavable as an integral unit, has an entirely sealed autoclavable optical assembly, has no internal moving optical components, is provided with an external focus adjustment sealed independently of the optical system, is characterized by an entirely reusable construction as a whole, has an image plane outside of the endoscope enclosure, is inexpensive to manufacture, easy to use, easy to assemble and disassemble, has an optical performance which is not affected in case of damage of the seals, and is compatible with a variety of existing external image-sensing devices.

Although the invention has been shown and described in detail with reference to specific practical examples, it is understood that these examples were given only for illustrative purposes and that the materials, shapes, configurations, and structural elements of the parts and units can be changed, provided these changes do not depart from the scope of the appended patent claims. For example, the physician may hold the CCD camera and focus the endoscope by rotating the driver. Although the focusable optical instrument of the invention was shown and described with reference to an endoscope, the principle of the invention is applicable to optical devices of other type such as a boroscope, veterinarian scope, etc.

We claim:

1. An endoscope comprising:
    a replaceable sealed optical assembly without moveable parts having a distal end, a proximal end, and an image plane located outside of said replaceable sealed optical assembly;
    a focusing device connected on one side to said proximal end and on the opposite side to an external image receiving device, said external image receiving device having an image receiving plane such that focusing of said endoscope is achieved when said image plane coincides with said image receiving plane;
    said focusing device having means for relative motion with respect to said replaceable sealed optical assembly, said means for relative motion comprising
        an internal driver in the form of a first tubular body slidingly fit onto said distal end of said replaceable sealed optical assembly, said internal driver having an external thread on its outer surface;
        an adapter made in the form of a second tubular body having an inner thread engaged with said external thread, said adapter having a proximal end and a distal end and being rigidly connected to said image receiving device on said proximal end;
        a focus driver in the form of a third tubular body which is rigidly connected to said sealed optical assembly and to said internal driver, so that rotation of said focus driver relative to said adapter will cause relative displacement of said image plane with respect to said image receiving plane.

2. The endoscope of claim 1, having sealing means between said internal driver and said sealed optical assembly, between said internal driver and said adapter, between said adapter and said focus driver, and between said focus driver and said sealed optical assembly.

3. The endoscope of claim 2, wherein said sealing means are O-rings.

4. The endoscope of claim 1, wherein said replaceable sealed optical assembly includes an image collecting element on said distal end and an image output element on said proximal end.

5. The endoscope of claim 4, wherein said external image receiving device is selected from a group consisting of a charge-coupled device camera and a still camera.

6. The endoscope of claim 5, wherein said image collecting element comprises an objective lens.

7. The endoscope of claim 6, further comprising an image delivery means located within said sealed encapsulated optical assembly between said image collecting element and said image output element.

8. The endoscope of claim 7, wherein said image-delivery means comprises at least one rod lens.

9. The endoscope of claim 7, wherein said image output element comprises a telescope.

10. The endoscope of claim 7, wherein said image-delivery means comprises an optical fiber.

11. The endoscope of claim 7, wherein said image-delivery means comprises a combination of elements selected from the group consisting of an optical fiber, an optical rod, and an optical lens.

12. The endoscope of claim 5, wherein said image output element comprises a telescope.

13. An endoscope for observation of an object in an enclosed area, comprising:
    a sealed encapsulated optical assembly without movable parts having a distal end and a proximal end;
    an objective on said distal end;
    an ocular on said proximal end;
    a focusing assembly on said proximal end having means for relative motion with respect to said sealed encapsulated optical assembly;
    an external image receiving device attached to said focusing assembly for moving therewith; and
    illuminating means for illuminating the object;

said sealed optical assembly having an image plane located outside of said sealed encapsulated optical assembly;

said external image receiving device having an image receiving plane, so that focusing of said endoscope is achieved when said image plane coincides with said image receiving plane;

wherein said means for relative motion comprises:

an internal driver in the form of a first tubular body slidingly fit onto said distal end of said replaceable sealed optical assembly, said internal driver having an external thread on its outer surface;

an adapter made in the form of a second tubular body having an inner thread engaged with said external thread, said adapter having a proximal end and a distal end and being rigidly connected to said image receiving device on said proximal end;

a focus driver in the form of a third tubular body which is rigidly connected to said sealed optical assembly and to said internal driver, so that rotation of said focus driver relative to said adapter will cause relative displacement of said image plane with respect to said image receiving plane.

14. The endoscope of claim 13, wherein said external image receiving device is a charge-coupled device camera.

15. The endoscope of claim 14, further comprising an image delivery means located within said sealed encapsulated optical assembly between said objective and said ocular.

16. The endoscope of claim 15, wherein said ocular comprises a telescope.

17. The endoscope of claim 15, wherein said image-delivery means is at least one of elements selected from the group consisting of an optical fiber, an optical rod, and an optical lens.

18. The endoscope of claim 13, having sealing means between said internal driver and said sealed optical assembly, between said internal driver and said adapter, between said adapter and said focus driver, and between said focus driver and said sealed optical assembly.

19. The endoscope of claim 18, wherein said sealing means are O-rings.

20. The endoscope of claim 13, wherein said illuminating means comprises a plurality of optical fibers extending from said distal to said proximal end of said sealed optical assembly.

21. A method of focusing an optical instrument, comprising the steps of:

providing said optical instrument with a replaceable sealed optical assembly without moveable parts and with a focusing device connected on one side to said replaceable sealed optical assembly and on the opposite side to an image receiving means, said replaceable sealed optical assembly having an image plane and said image-receiving means having an image-receiving plane;

wherein said focusing device having means for relative motion with respect to the replaceable sealed optical assembly, said means for relative motion comprising:

an internal driver in the form of a first tubular body slidingly fit onto said distal end of said sealed optical assembly, said internal driver having an external thread on its outer surface;

an adapter made in the form of a second tubular body having an inner thread engaged with said external thread, said adapter having a proximal end and a distal end and being rigidly connected to said image receiving device on said proximal end;

a focus driver in the form of a third tubular body which is rigidly connected to said sealed optical assembly and to said internal driver, so that rotation of said focus driver relative to said adapter will cause relative displacement of said optical plane with respect to said image-receiving plane;

changing a distance between said image plane and said image receiving plane while maintaining said replaceable sealed optical assembly immobile and moving said image-receiving means; and superposing said image plane onto said image-receiving plane thus focusing said optical instrument.

22. The method of claim 21, wherein said optical instrument is endoscope.

23. The method of claim 21, wherein said image-receiving means is a charge-coupled device camera.

24. The method of claim 22, wherein said image-receiving means is a charge-coupled device camera.

* * * * *